US010898069B1

(12) United States Patent
Ramdoo (10) Patent No.: US 10,898,069 B1
(45) Date of Patent: Jan. 26, 2021

(54) OPTICAL APPARATUS (71) Applicant: Tympa Health Technologies Ltd., London (GB)

(72) Inventor: Krishan Ramdoo, London (GB)

(73) Assignee: Tympa Health Technologies Ltd., London (GB)

( * ) Notice: Subject to any disclaimer, the term of this patent is extended or adjusted under 35 U.S.C. 154(b) by 0 days.

(21) Appl. No.: 16/823,657

(22) Filed: Mar. 19, 2020

(30) Foreign Application Priority Data

Nov. 19, 2019 (GB) .................................. 1916848.3

(51) Int. Cl.
*A61B 1/227* (2006.01)
*G02B 15/14* (2006.01)
*G02B 13/00* (2006.01)

(52) U.S. Cl.
CPC .......... *A61B 1/227* (2013.01); *G02B 13/0035* (2013.01); *G02B 15/143* (2019.08)

(58) Field of Classification Search
CPC ... A61B 1/227; G02B 15/143; G02B 13/0035
USPC .......................................................... 600/200
See application file for complete search history.

(56) References Cited

U.S. PATENT DOCUMENTS

| 2012/0245422 | A1* | 9/2012 | Hasbun .................. | A61B 1/227 600/200 |
| 2013/0128223 | A1* | 5/2013 | Wood ................. | A61B 1/00186 351/206 |
| 2014/0206979 | A1 | 7/2014 | Berkner et al. | |
| 2016/0249805 | A1* | 9/2016 | Salvati ................. | A61B 1/0684 351/206 |
| 2016/0338587 | A1 | 11/2016 | Gupta | |
| 2016/0338590 | A1* | 11/2016 | Sagalovich .......... | A61B 1/0684 |
| 2018/0168440 | A1* | 6/2018 | Das ........................ | G06T 15/50 |
| 2018/0210173 | A1 | 7/2018 | Blahnik et al. | |
| 2019/0216402 | A1* | 7/2019 | Sayani .................. | G16H 10/60 |

FOREIGN PATENT DOCUMENTS

| EP | 3437549 A1 | 2/2019 |
| GB | 2569325 A | 6/2019 |
| JP | 2002034916 A | 5/2002 |
| WO | 2013071153 A1 | 5/2013 |

OTHER PUBLICATIONS

United Kingdom Combined Search and Examination Report for GB Application No. 1916848.3, dated Dec. 20, 2019, 7 pages.

* cited by examiner

*Primary Examiner* — Eduardo C Robert
*Assistant Examiner* — David C Comstock
(74) *Attorney, Agent, or Firm* — Tucker Ellis LLP; Michael G. Craig (57) ABSTRACT There is described an apparatus comprising a first optical element, a second optical element and a spacing element for use with a mobile user device. The first optical element is configured to provide an image of an object to an intermediate image plane and the second optical element magnifies the image to provide a final image in a final image plane in which a camera aperture of the device is supported. The spacing element maintains a fixed separation between the object and the first optical element. Image magnification is achieved while also providing a space for tool access. Mirrors may be used to divert the optical path, allowing the optical path to be folded for more compact apparatus. A third optical element disposed at the intermediate image plane may be used to reduce vignetting effects in the final image.

19 Claims, 10 Drawing Sheets

OPTICAL APPARATUS

CROSS-REFERENCE TO RELATED APPLICATIONS

This application claims priority to United Kingdom Patent Application No. 1916848.3, entitled OPTICAL APPARATUS, filed Nov. 19, 2019, which is incorporated herein by reference.

BACKGROUND

The present application relates an apparatus for providing magnification of an object for a device having a camera. In particular, embodiments are directed to apparatus for medical visual examination and to apparatus for assisting a user in performing medical procedures. In particular, the application relates to an instrument configured for use with a mobile user device, providing enhanced image quality while maintaining sufficient access for tools.

Existing instruments for medical diagnosis rely on visual or photographic examination. In general, they provide a means of observing, in real-time, a magnified image of a subject anatomical structure. Some examinations are often coupled with procedures for which tool access is required, such as removing ear wax from the outer ear canal. Detailed visualisation of the structures being examined is critical for both accurate diagnosis and minimising potential pain or damage caused during the procedures. Performing procedures with simultaneous visualisation of the subject structures further increases the quality of care provided, offering the ability to record the whole process for subsequent analysis. Such apparatus is expensive and difficult to operate.

Some instruments incorporate traditional optical systems with mobile user devices, providing improved ergonomics, usability and cost for wider access to associated procedures such as micro-suction of the ear canal. However, such instruments often exhibit poor image magnification and detail, and do not provide sufficient space for tool access.

GB-A-2569325 discloses a handle, a speculum mount, a smartphone mount and a spacing element. The spacing element is configured to maintain an optical separation distance between the speculum mount and the smartphone mount. The apparatus also comprises optical paths for the smartphone's camera and light source and optical elements to focus the image and/or direct the light. The optical element may be configured to provide dual images to the smartphone's camera. In use the apparatus enables a clear view of the ear canal while allowing access of a micro-suction tool to be inserted into the ear canal. A cannula grip and guide for the micro-suction tool is also disclosed.

SUMMARY

Aspects of the invention are set out in the independent claims and preferred features are set out in the dependent claims.

There is described herein apparatus for providing magnification of an object for a device having a camera, the apparatus comprising:

a first optical element arranged at a first location to provide an image of the object in an intermediate image plane; and a second optical element arranged at a second location to magnify optically the intermediate image to provide a final image in a final image plane;

means for mounting the apparatus in a fixed position relative to the device such that a camera aperture of the device is supported in the final image plane;

a spacing element for maintaining the first optical element at a fixed distance from the object;

wherein the intermediate image plane and the second optical element are arranged along an optical path extending between the first optical element and the final image plane;

wherein the second optical element is disposed on the optical path between the intermediate image plane and the final image plane;

wherein a first distance along the optical path from the intermediate image plane to the final image plane is significantly smaller than a second distance along the optical path from the first optical element to the intermediate image plane.

The apparatus can provide greatly increased magnification of objects undergoing examination, while providing clear space for tool access to the objects. In particular, the use of two optical elements arranged as described significantly increases the magnification of the object while the spacing element maintains the object at a fixed distance from the first optical element thus allowing a space for tool access to be provided.

The second distance may be at least twice the first distance and preferably around 5 times larger than the first distance. Alternatively, the second distance may be at least around a decimal order of magnitude greater than the first distance. It is noted that the distance along the optical path may be significantly greater than the physical straight-line distance, in particular if the optical path is bent and diverted as described in more detail below.

While the device may simply comprise a camera and hardware and software for operating the camera, optionally, the device having a camera comprises a mobile user device such as a smartphone or tablet device. It may also comprise a custom device that includes a camera, hardware and software and optionally a screen and wireless communication capabilities.

The apparatus may further comprise a body for defining an aperture through which human or animal anatomical structures are examined. The optical path preferably passes through the aperture. The body may be a speculum for placing in a patient's ear canal. The apparatus may comprise an otoscope. The speculum may be disposed at the distal end of the spacing element, and the spacing element may be configured to provide a gap for tool access to the ear canal through the speculum.

The apparatus may further comprise a third optical element disposed on the optical path at the intermediate image plane. The third optical element may contain the entire image at the intermediate image plane, and may be arranged such that the first optical element and the second optical element lie in conjugate planes. Advantageously, this feature reduces in the final image vignetting effects resulting from light at higher field angles missing the second optical element.

At least one, preferably each, optical element may comprise a lens. The first optical element may comprise two doublets.

The apparatus may further comprise an aperture stop disposed on the optical path, wherein the aperture stop effects a reduction in the diameter of the entrance pupil of the apparatus, optionally wherein the first optical element comprises two doublets and the aperture stop is disposed between the two doublets. This increases the depth of field in the final image by increasing the f-number of the optics.

The apparatus may further comprise a mirror arrangement comprising a plurality of mirrors arranged to divert the optical path away from and then towards an axis extending between the first optical element and the final image plane, such that the optical path is longer than the distance between the first optical element and the final image plane. The plurality of mirrors may divert the optical path to a plane substantially parallel and proximate to a distal surface of the device, that is, along a path parallel to the back of the mobile device. This offers the advantage of being able to fold a section of the optical path, providing a more compact and ergonomic apparatus while maintaining sufficient clear space for tool access.

The first optical element may be achromatic. The front focal length of the first optical element may be no less than around 80 mm, preferably no less than 100 mm. The front focal length of the first optical element may be no greater than around 180 mm, preferably no greater than 150 mm. The power of the second optical element may be no less than around 3 dioptres, preferably no less than 5 dioptres. The power of the second optical element may be no greater than around 25 dioptres, preferably no greater than 23 dioptres. The optical magnification factor of the apparatus may be no less than around 8, preferably no less than 11. It is noted that 1 dioptre=1 $m^{-1}$.

The apparatus may further comprise a lighting arrangement, comprising a powered light source, preferably a plurality of white light LEDs. The apparatus may further comprise an optical arrangement configured to guide light from the powered light source towards the object. The powered light source may be provided by the device, for example it may be the flash light associated with the camera of the device. The lighting arrangement may further comprise electronic circuitry for controlling the powered light source and further comprise means for attaching the powered light source and the electronic circuitry to the spacing element, wherein the optical arrangement comprises a collimator. Advantageously, the lighting configuration increases the illumination of the final image for better image quality. The apparatus may further comprise a power source for powering the light source, preferably a rechargeable lithium-ion battery, and further comprise electronic circuitry for controlling the power source. The apparatus may further comprise a handle. The power source and electronic circuitry for controlling the power source may be disposed in the handle.

An accompanying application may be provided for the mobile computing device having a camera receiving an image from the apparatus described above and such an application may be configured to crop the image, digitally magnify the image and/or invert the image in real-time.

The application may be further configured to control and set other parameters associated with the system. For example, it may be arranged to control the intensity, frequency and beam width of the powered light source and control the diameter of one or more apertures in the apparatus.

According to another aspect, there is described herein a method for magnifying an object for a device having a camera, the method comprising the steps of:

arranging a first optical element at a first location to provide an image of the object in an intermediate image plane; and arranging a second optical element at a second location to magnify optically the intermediate image to provide a final image in a final image plane;

mounting the first and second optical elements in a fixed position relative to the device such that a camera aperture of the device is supported in the final image plane;

maintaining the first optical element at a fixed distance from the object through use of a spacing element;

wherein the intermediate image plane and the second optical element are arranged along an optical path extending between the first optical element and the final image plane;

wherein the second optical element is disposed on the optical path between the intermediate image plane and the final image plane;

wherein a first distance along the optical path from the intermediate image plane to the final image plane is significantly smaller than a second distance along the optical path from the first optical element to the intermediate image plane.

As noted above, embodiments can enable greatly increased magnification of objects undergoing examination, while providing clear space for tool access to the objects.

The method may further comprise the step of arranging a third optical element on the optical path in the intermediate image plane, the third optical element containing the entire image at the intermediate image plane and being arranged such that the first optical element and the second optical element lie in conjugate planes.

The method may further comprise the step of arranging a plurality of mirrors to divert the optical path away from and then towards an axis extending between the first optical element and the final image plane, such that the optical path is longer that the distance between the first optical element and the final image plane. The method may further comprise the step of arranging the plurality of mirrors to divert the optical path to a plane substantially parallel and proximate to a distal surface of the device. The method may further comprise the step of installing the optical elements and the plurality of mirrors in a housing, wherein the housing is partially or totally sealed and provides space for the optical path through one or more internal cavities.

The method may further comprise the step of illuminating the object using a powered light source and an associated optical arrangement, the light source preferably being a plurality of white light LEDs. The powered light source may be provided by the device. The method may further comprise the steps of controlling the powered light source using electronic circuitry and attaching the electronic circuitry to the spacing element. The method may further comprise coupling a handle to the spacing element. The method may further comprise powering the powered light source using a power source and associated electronic circuitry. The power source and the associated electronic circuitry may be disposed in the handle.

Any system feature as described herein may also be provided as a method feature, and vice versa. As used herein, means plus function features may be expressed alternatively in terms of their corresponding structure.

Any feature in one aspect of the invention may be applied to other aspects of the invention, in any appropriate combination. In particular, method aspects may be applied to system aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

DESCRIPTION OF THE DRAWINGS

Embodiments of the present invention will now be described by way of example only and with reference to the accompanying drawings, in which:

FIG. 2e shows a perspective distal end view of an example apparatus according to the embodiment of FIG. 2a;

DETAILED DESCRIPTION

Figure 1A:
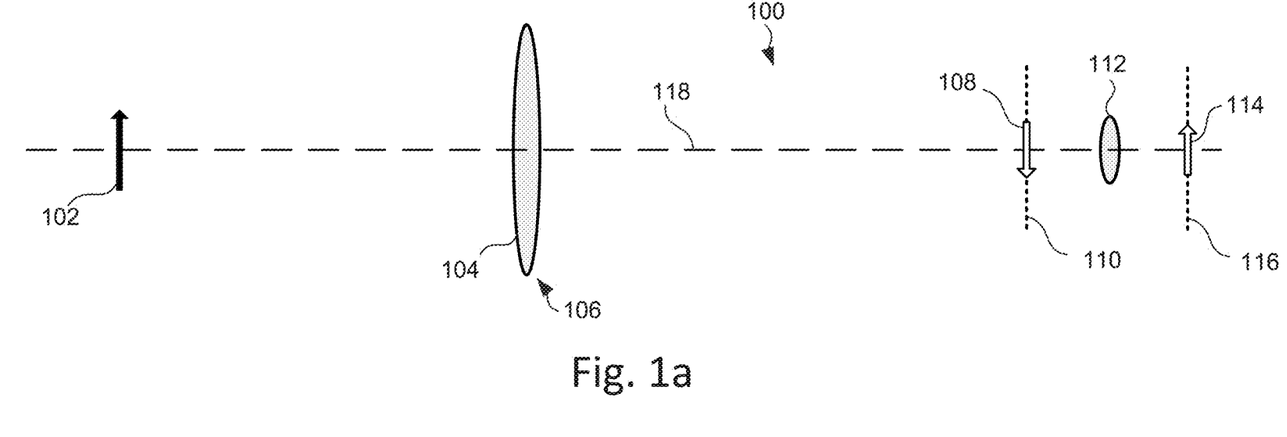
FIG. 1a shows a schematic side view of apparatus comprising first and second optical elements.
Figure 1B:
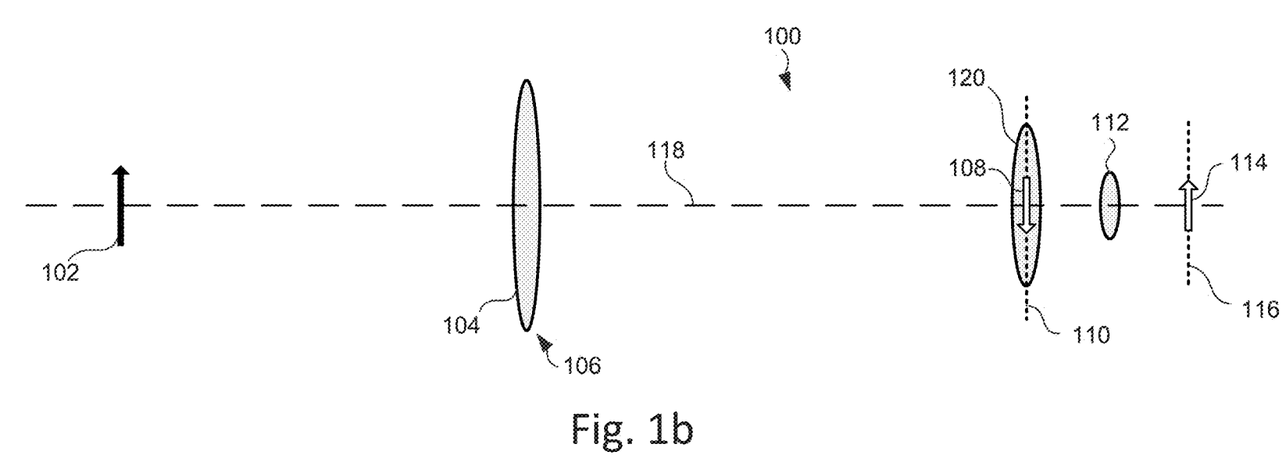
FIG. 1b shows the schematic side view of FIG. 1a further comprising a third optical element.

Referring to FIGS. 1a and 1b, apparatus 100 for providing magnification of an object 102 for a device, in this embodiment a mobile user device, having a camera according to a first embodiment will now be described. The apparatus comprises a first optical element 104 at a first location 106, and a second optical element 112. The first optical element 104 provides an image 108 of the object 102 in an intermediate image plane 110. The image 108 is then magnified optically by the second optical element 112 to provide a final image 114 in a final image plane 116. The intermediate image plane 110 and the second optical element 112 are arranged along an optical path 118 extending between the first optical element 104 and the final image plane 116. The focal lengths of the optical elements 104, 112 are such that the distance from the first optical element 104 to the intermediate image plane 110 is greater than the distance from the intermediate image plane 110 to the second optical element 112.

As shown in FIG. 1b, a third optical element 120 may be provided at the intermediate image plane 110, such that the third optical element 120 contains the entire image 108. The third optical element 120 is arranged such that the first optical element 104 and the second optical element 112 lie in conjugate planes.

In both embodiments, a spacing element (not shown in FIG. 1a or 1b) maintains a fixed separation between the first optical element 104 and the object 102. Means for mounting the apparatus 100 in a fixed position relative to the mobile user device is provided (also not illustrated in FIG. 1a or 1b) such that a camera aperture of the mobile user device is supported in the final image plane 116. At least one, preferably each, optical element is a lens or a system of lenses.

The length of the optical path 118 taken between two locations will be referred to as a distance along the optical path 118, and is distinct from the shortest spatial distance between the two locations. The distance along the optical path 118 from the intermediate image plane 110 to the final image plane 116 is significantly smaller than the distance along the optical path 118 from the intermediate image plane 110 to the first optical element 104.

It is noted that FIGS. 1a and 1b are not drawn to scale and the distance between the first optical element 104 and the plane of the object 102 may be greater than the spatial distance between the optical elements 104, 112 and the spatial distance between the first optical element 104 and the image plane 116. That is, the spacing element is arranged to provide a gap large enough to allow access for surgical tools or other devices.

For the avoidance of doubt, the end of the apparatus 100 nearest to the object 102 will be referred to as the distal end, i.e. the end which is furthest from the user, and the end of the apparatus 100 nearest to the mobile user device will be referred to as the proximal end, i.e. the end closest to the user.

The second optical element 112 is arranged to reduce the minimum focusing distance (and effective focal length) of the camera, allowing the image 108 to be placed closer to the final image plane 116 for an in-focus final image 114.

The apparatus 100 may be used for medical examinations and any coupled procedures. Accordingly, by way of example, the apparatus 100 may be incorporated into or implemented in conjunction with medical devices such as otoscopes, endoscopes or ophthalmoscopes, for examination of internal or external anatomical structures.

In one example, the first optical element 104 has a focal length of approximately 100 mm –150 mm and is placed along the optical path 118 approximately one focal length away from the object 102. The intermediate image plane 110 is therefore approximately 300 mm along the optical path 118 from the first optical element 104. As in this example, magnification can be achieved using the first optical element 104, found as the ratio of the distances along the optical path 118 from the first optical element 104 to the object 102 and from the first optical element 104 to the intermediate image plane 110. The second optical element 112 has a power of approximately 10 dioptres and reduces the minimum focusing distance of the camera by a factor of 1.6, and in combination with the first optical element 104 has a magnification factor of approximately 3.2 (equal to 2×1.6 where the ratio of the distance between the object 102 and the first optical element 104 to the distance between the first optical element 104 and the intermediate image plane 110 is 2:1). Alternatively, if the power of the second optical element 112 is 23 dioptres, the minimum focussing distance is reduced by a factor of approximately 2.4 and a magnification factor of approximately 4.8 is achieved. Advantageously, compared to using a camera alone at a similar separation from the object 102, this apparatus 100 achieves a magnification approximately 8 times greater with a 10-dioptre second optical element 112 and approximately 11 times greater with a 23-dioptre second optical element 112.

Figure 2A:
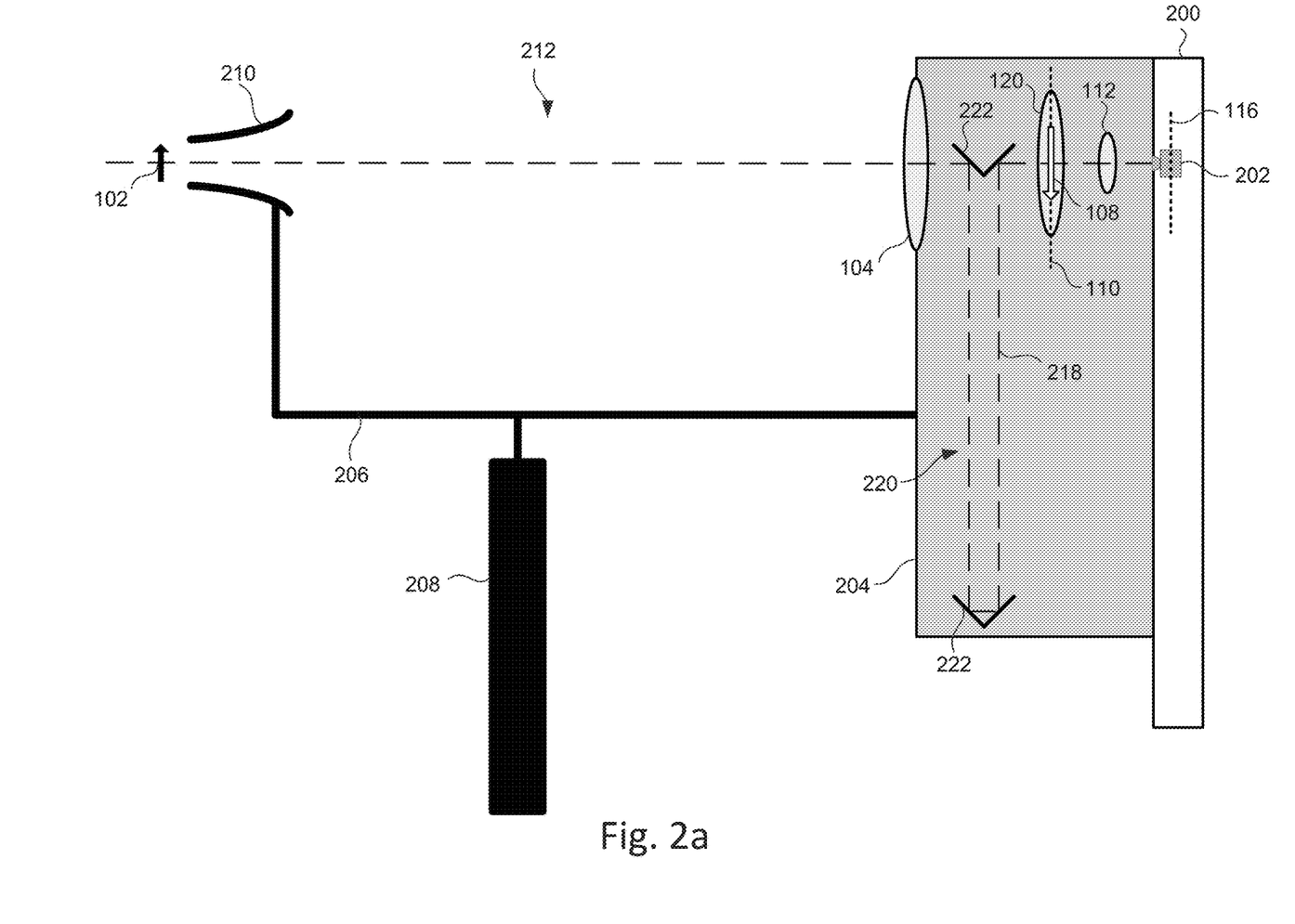
FIG. 2a shows a schematic side view of the apparatus of FIG. 1b with the optical path diverted by a mirror arrangement.

Referring to FIG. 2a, apparatus 100 comprising an otoscope according to a second embodiment will now be described. The means for mounting the apparatus 100 in a fixed position relative to the mobile user device 200 comprises a housing 204 from which the spacing element 206 extends distally. A handle 208 and a speculum 210 are coupled to the spacing element 206, the speculum 210 defining an aperture through which human or animal anatomical structures, such as a patient's ear canal, may be examined. The speculum 210 is disposed on the distal end of the spacing element 206 and is placed in a patient's ear canal during operation of the apparatus 100. This provides a fixed separation between the object 102 (ear canal) and the first optical element 104. The gap 212 is sufficiently large for tool access to the ear canal through the speculum 210, suitable for medical procedures such as micro-suction.

Figure 2B:
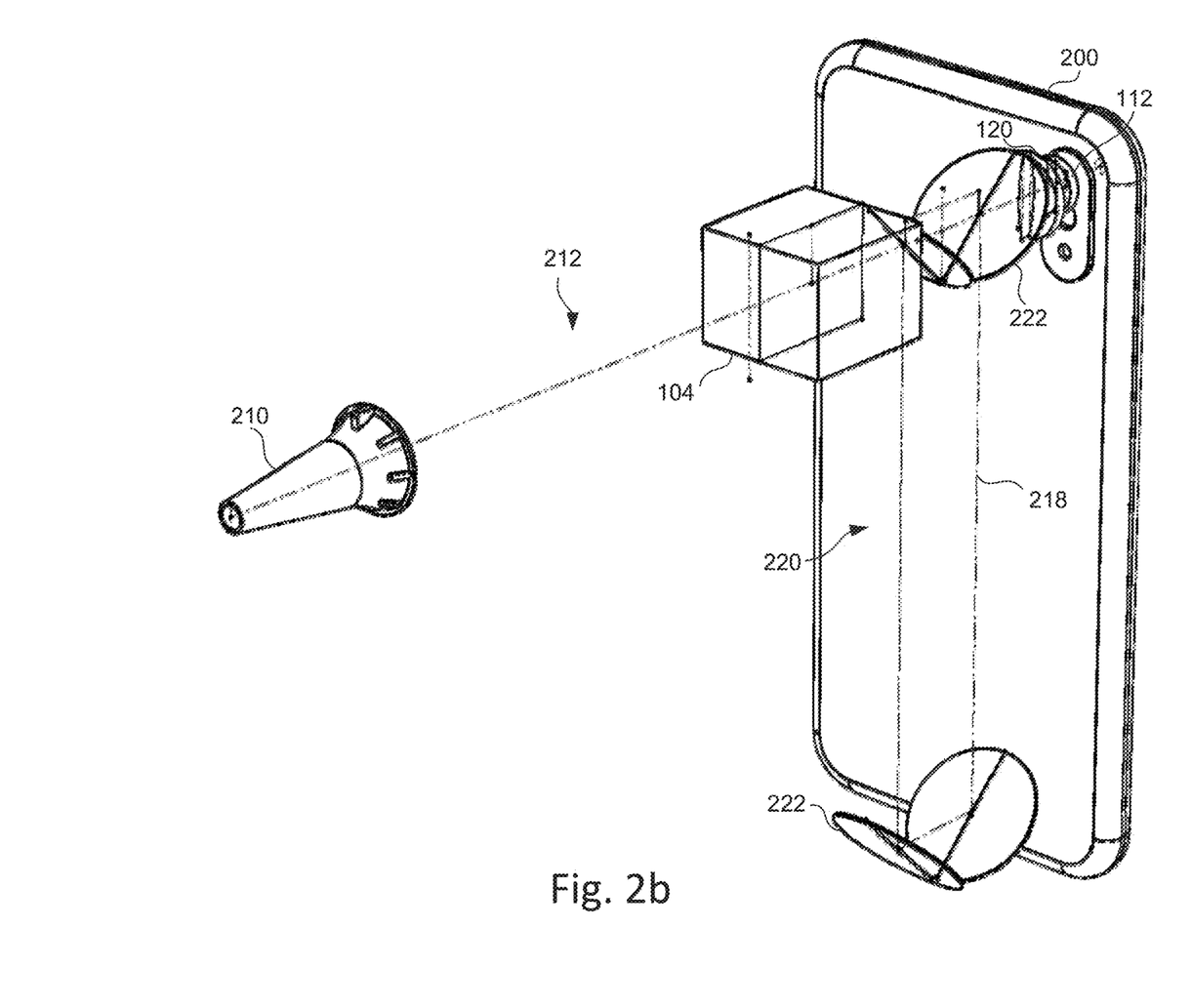
FIG. 2b shows a perspective distal end schematic view of the apparatus of FIG. 2a according to one embodiment.

The apparatus 100 further comprises a mirror arrangement 220 comprising a plurality of mirrors 222 to divert the optical path 218 away from and then towards an axis extending between the first optical element 104 and the final image plane 116. Accordingly, the optical path 218 is longer than the distance between the first optical element 104 and the final image plane 116. The plurality of mirrors 222 is preferably a plurality of plane mirrors, for example of about 10 or 12.5 mm diameter. An aperture of the camera 202 is shown supported in the final image plane 116 in FIG. 2a. In one example corresponding to FIGS. 2a, 2b and 2e, the bounding dimensions of the housing 204 are approximately 80 mm×30 mm×170 mm.

Figure 2C:
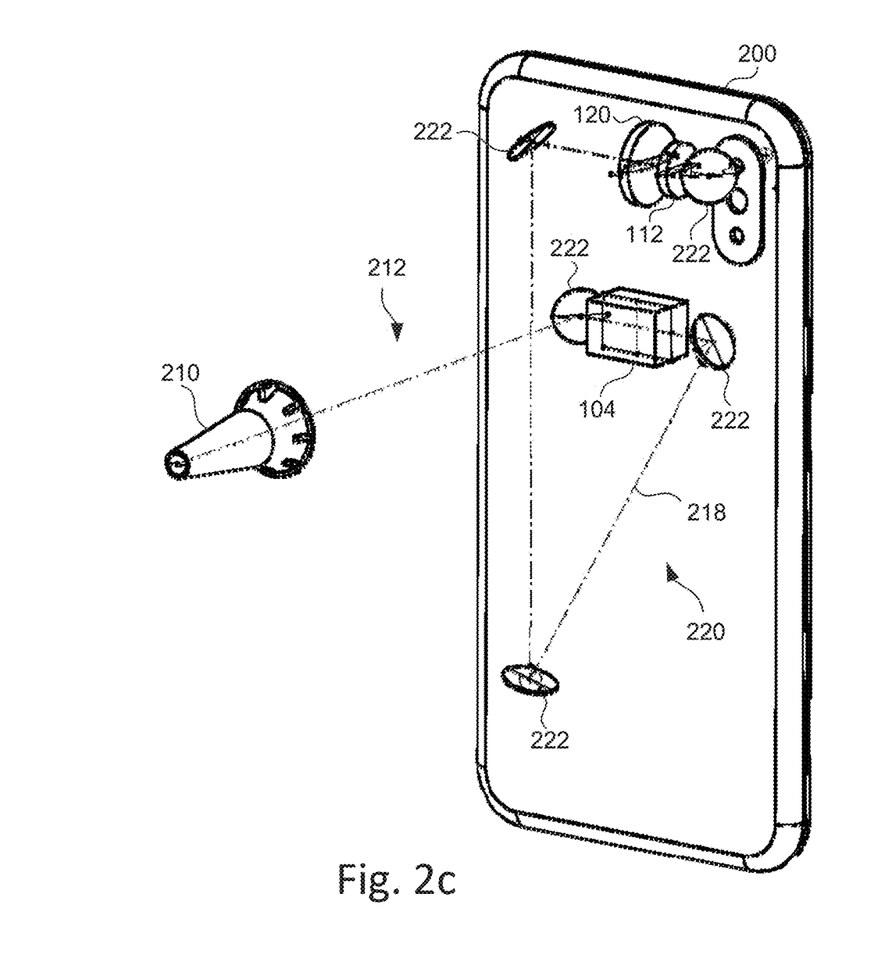
FIG. 2c shows a perspective distal end schematic view of the apparatus of FIG. 2a according to an alternative embodiment.
Figure 2D:
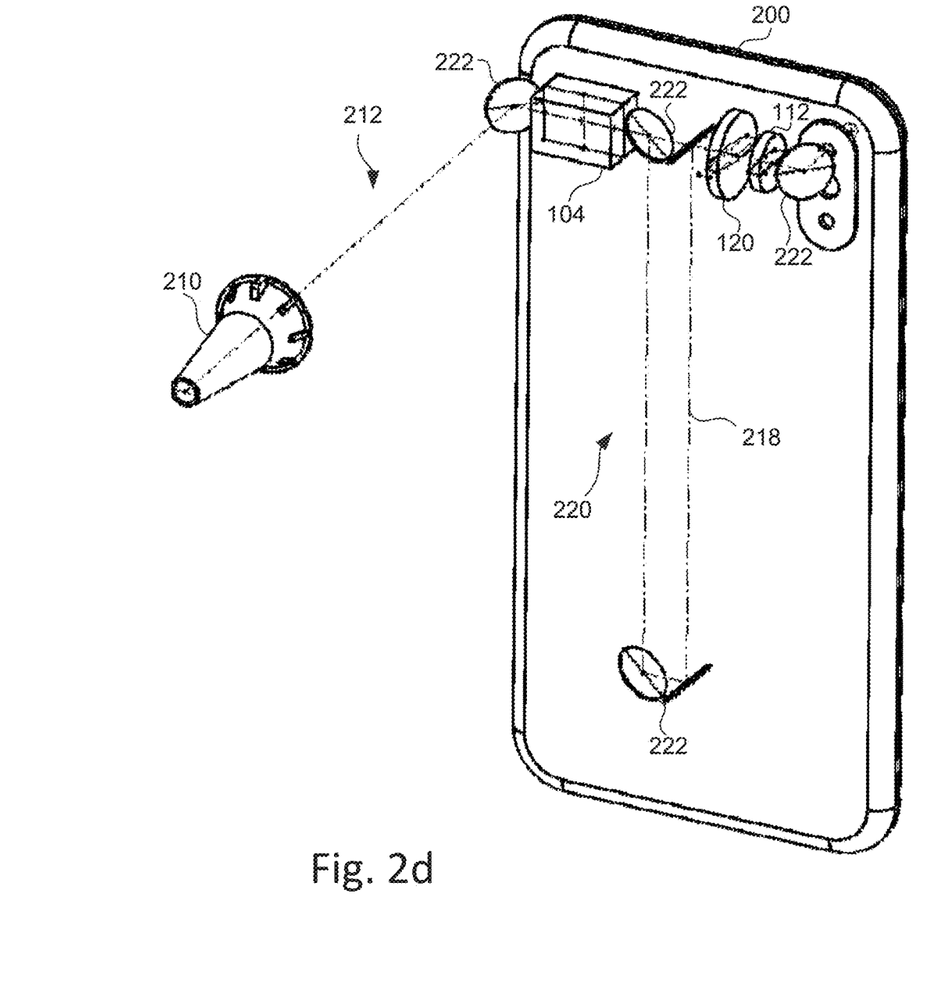
FIG. 2d shows a perspective distal end schematic view of the apparatus of FIG. 2a according to a further alternative embodiment.
Figure 2E:
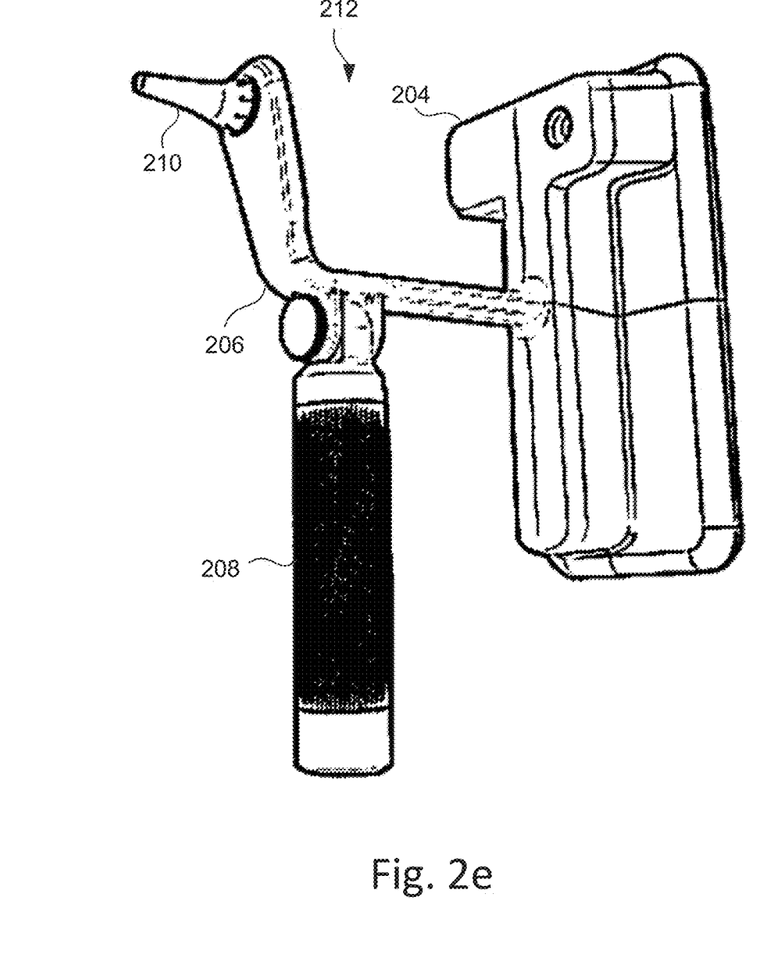

As shown in FIG. 2c, the plurality of mirrors 222 may divert the optical path 218 to a plane substantially parallel and proximate to a distal surface (that is the rear surface) of the mobile user device 200. A number of other folding arrangements exist, for example a further arrangement is shown in FIG. 2d. In the example of FIG. 2c, the bounding dimensions of the housing 204 are approximately 20 mm×50 mm×120 mm.

Figure 3:
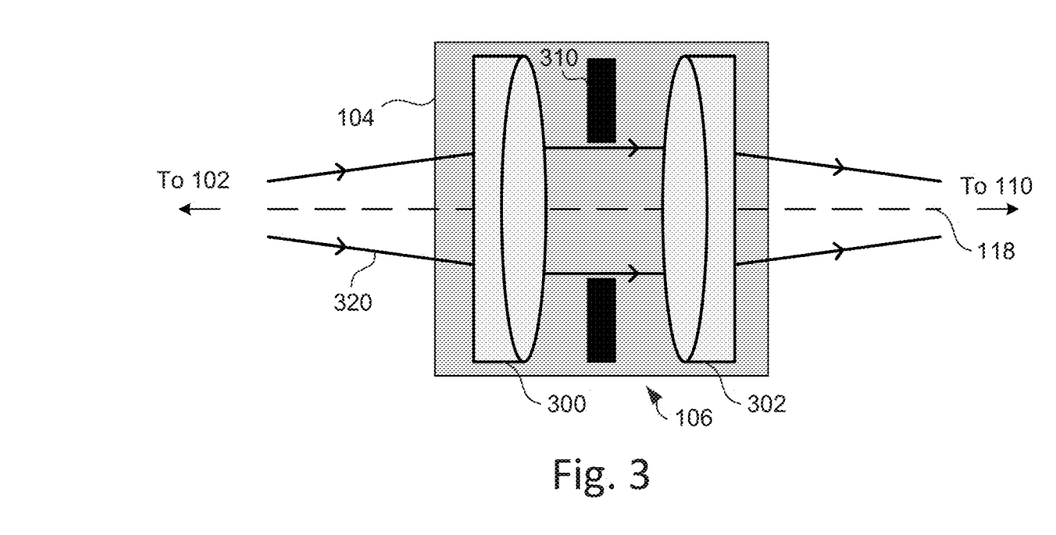
FIG. 3 shows a schematic side view of a first optical element according to an exemplary embodiment.

Referring to FIG. 3, the first optical element 104 in the apparatus 100 according to an alternative embodiment will now be described. In this embodiment, the first optical element 104 comprises two achromatic doublets 300, 302 arranged in opposing orientations. As illustrated in FIG. 3 by example light rays 320, the achromatic doublets 300, 302 have one infinite conjugate, meaning the light rays 320 form a collimated beam between the achromatic doublets 300, 302. Using the achromatic doublets 300, 302 reduces achromatic aberrations that could give rise to colour fringing artefacts. The performance of the achromatic doublets 300, 302 is diffraction limited provided the apparatus 100 has field angles less than around 5 degrees, meaning other common forms of aberrations are reduced, such as spherical aberrations, coma and astigmatism. The achromatic doublets 300, 302 may be non-identical, wherein their focal lengths (equivalent to the front and rear focal lengths of the first optical element 104 respectively) are different according to the respective distances of the object 102 and the intermediate image plane 110 from the first optical element 104.

The first optical element 104 further comprises an aperture stop 310 disposed in between the achromatic doublets 300, 302. The aperture stop 310 effects a reduction in the diameter of the entrance pupil of the apparatus 100, wherein the entrance pupil is the smallest optical aperture in the apparatus 100 along the optical path 118. This has the effect of increasing the f-number of the apparatus 100, i.e. the ratio of its focal length to the diameter of the entrance pupil. The depth of field in the final image 114 is reduced as a result of magnification. To compensate, greater depth of field is achieved by increasing the f-number. In some embodiments, the diameter of the aperture stop 310 may be adjustable between a plurality of different sizes.

In one example, the distal 300 and proximal 302 achromatic doublets both have an effective focal length of 100-150 mm and are separated from each other by a gap of 1 mm. The aperture stop 310 has an aperture diameter of 6.3 mm. The third optical element 120 has an effective focal length of 30 mm and is disposed around 148 mm proximally along the optical path 118 from the proximal achromatic doublet 302. The second optical element 112 has an optical power of 12.5 dioptres, and is disposed around 30 mm proximally along the optical path 118 from the third optical element 120 and 1 mm distally along the optical path 118 from the final image plane 116. The plane of closest focus exists around 147 mm distally from the distal achromatic doublet 300 and 5 mm from the distal end of the speculum 210; at the plane of closest focus the depth of field is 2 mm and the f-number is 3. The plane of furthest focus exists 17 mm distally from the plane of closest focus; at the plane of furthest focus the depth of field is 2.6 mm. The optical elements 104, 112, 120 in this example are of diameter 12.5 mm. The optical properties of the apparatus 100 can be designed to match the particular optics of a particular mobile user device. This allows the quality of the final image 114 to be tuned appropriately, especially with reference to depth of field and focus range.

In a similar example, the aperture stop 310 has an aperture diameter of 3 mm and the optical elements 104, 112, 120 have a diameter of 8 mm. In this example, the plane of closest focus exists 5 mm from the distal end of the speculum 210, and the plane of furthest focus exists 16.8 mm distally from the plane of closest focus. The depths of field at the plane of closest and furthest focus are, respectively, 7.7 mm and 9.6 mm. The f-number at the plane of closest focus is 6.3.

Figure 4A:
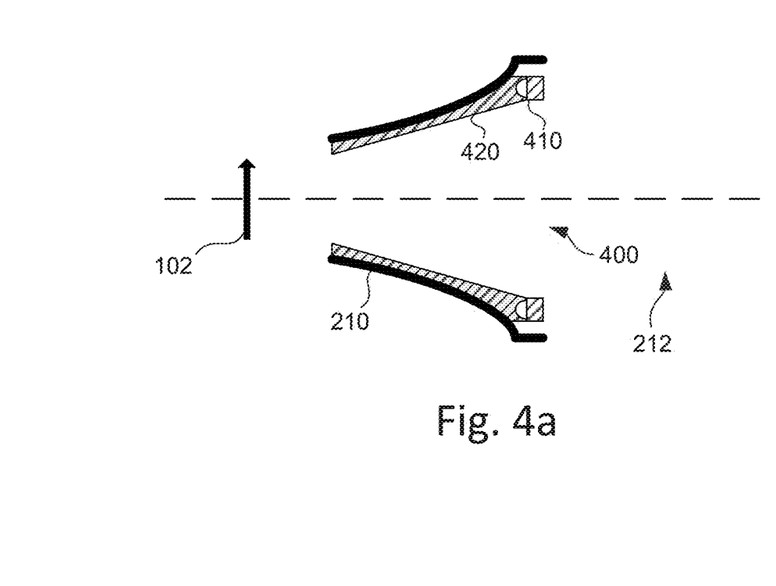
FIG. 4a shows a schematic cross-sectional side view of a lighting arrangement according to a first example.
Figure 4B:
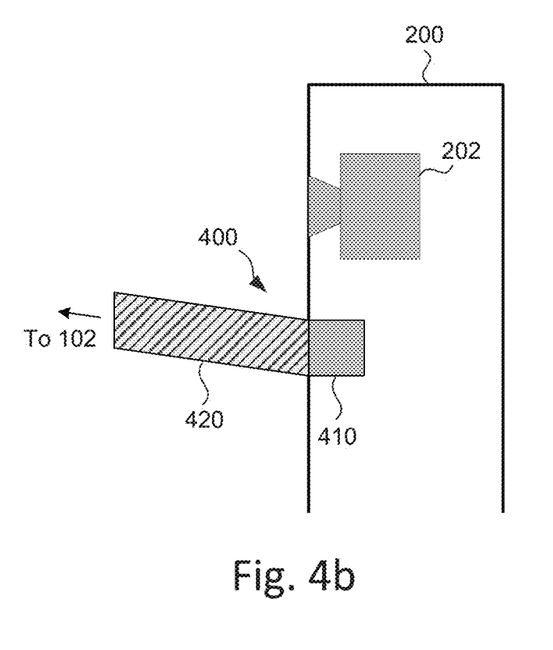
FIG. 4b shows a schematic cross-sectional side view of a lighting arrangement according to a second example.
Figure 5A:
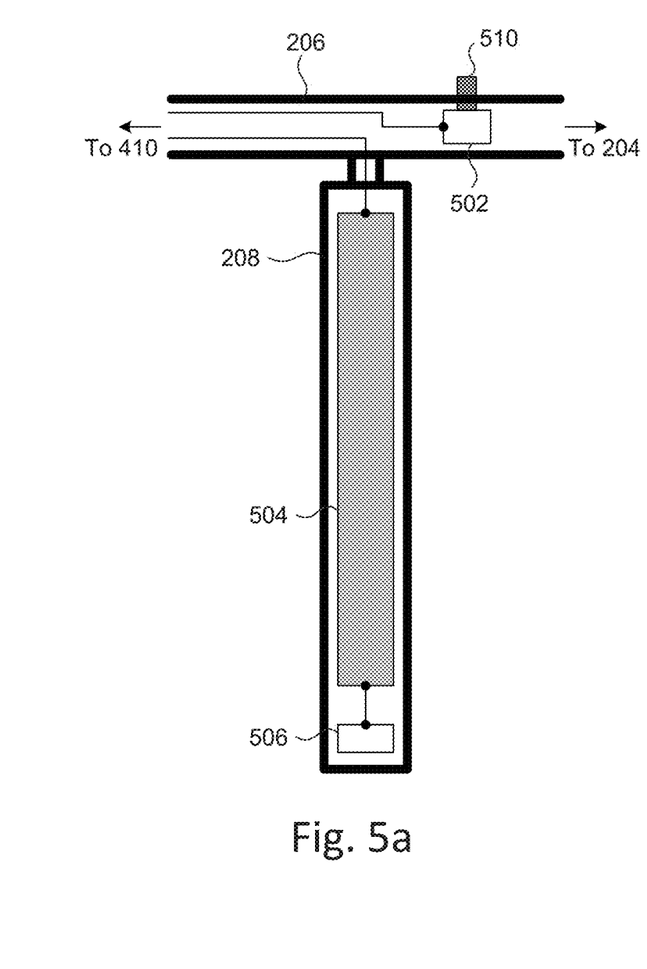
FIG. 5a shows a schematic cross-sectional side view of an embodiment of the handle of apparatus according to FIG. 2.
Figure 5B:
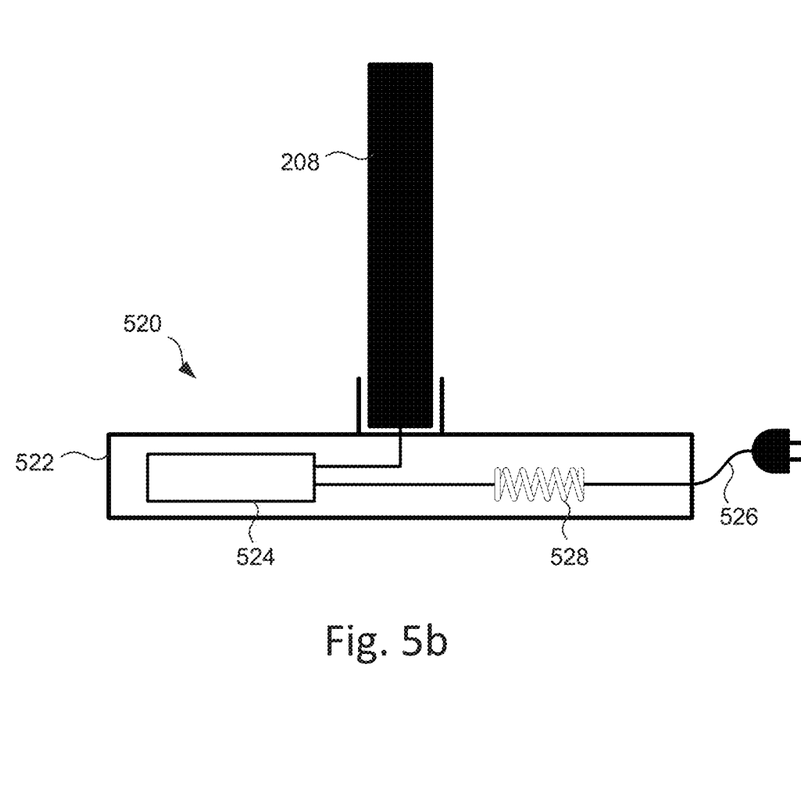
FIG. 5b shows a schematic cross-sectional side view of an associated charging stand according to one embodiment.

Referring to FIGS. 4 and 5, the apparatus 100 further comprises a lighting arrangement 400 according to a preferred embodiment which will now be described. The lighting arrangement 400 comprises a powered light source 410 and an optical arrangement 420 configured to guide light from the powered light source 410 towards the object 102. The lighting arrangement 400 is mounted to the apparatus 100, for example in the speculum (see FIG. 4a) or substantially adjacent to the mobile user device 200 (see FIG. 4b). As in FIG. 4b, the powered light source 410 is provided by the mobile user device 200; otherwise, the powered light source 410 is a plurality of white light LEDs. The optical arrangement 420 is a collimator for collimating the light emitted from the powered light source 410. Directing additional light to the object 102 in this way increases the illumination of the object 102 in the final image 114, providing good image quality despite parts of the apparatus 100 which may reduce the available light, such as the aperture stop 310.

The lighting arrangement 400 further comprises electronic circuitry 502 for controlling the powered light source 410, and means for attaching the powered light source 410 and electronic circuitry 502 to the apparatus 100 including positioning internal to parts mentioned above. The lighting arrangement 400 further comprises a power source 504 for powering the light source 410, and electronic circuitry 506 for controlling the power source, the power source 504 preferably being a rechargeable lithium-ion battery. Additionally, the apparatus 100 comprises a charging stand In one example, as shown in FIGS. 4a, 5a and 5b, the lighting arrangement 400 is disposed in the speculum 210. In this arrangement, the powered light source 410 comprises a ring of white light LEDs disposed on a circular printed circuit board extending around a circumference of the speculum 210. The optical arrangement 420 extends around a section of the internal contour of the speculum 210 and is coupled to the powered light source 410 to direct light along the length of the speculum 210 towards the object 102. Electronic circuitry 502 and a user-operable button 510 for activating the powered light source 410 are disposed in the spacing element 206. The power source 504 and its associated circuitry 506 are disposed in the handle 208, providing a counterweight to the mobile user device 200. The skilled person will appreciate that other arrangements of the light source and its associated power source may be provided.

As shown in FIG. 5b, a charging stand 520 is configured to receive the handle 208 of the apparatus 100 in order to charge the power source 504. The charging stand 520 comprises a charging stand cover 522 and a cabling 526 for connection to an external power supply, wherein the cabling 526 is coupled to the charging stand 520 via a cable retraction system 528 for biasing mechanically the cabling 526 towards the cover 522. For example, the cabling retraction system 528 may comprise a plurality of springs and pulleys. Electronic circuitry 524 for controlling the charging of the power source 504 is disposed within the charging stand 520. The charging stand 520 therefore provides a means for charging the power source 504 of the apparatus 100.

In the above embodiments of the apparatus 100, the optical elements 104, 112, 120 may be further configured to provide a stereoscopic final image 114, for example via one or more arrangements of mirrors, lenses and/or prisms. The camera 202 may be a stereo camera and the mobile user device 200 may comprise built-in hardware for displaying such stereoscopic images, for example an autostereoscopic screen. Alternatively, the mobile user device 200 may be coupled to suitable external viewing hardware for the user, such as binocular spectacles. Advantageously, this allows the user to view dual 2D images of the object 102, providing depth perception.

Figure 6:
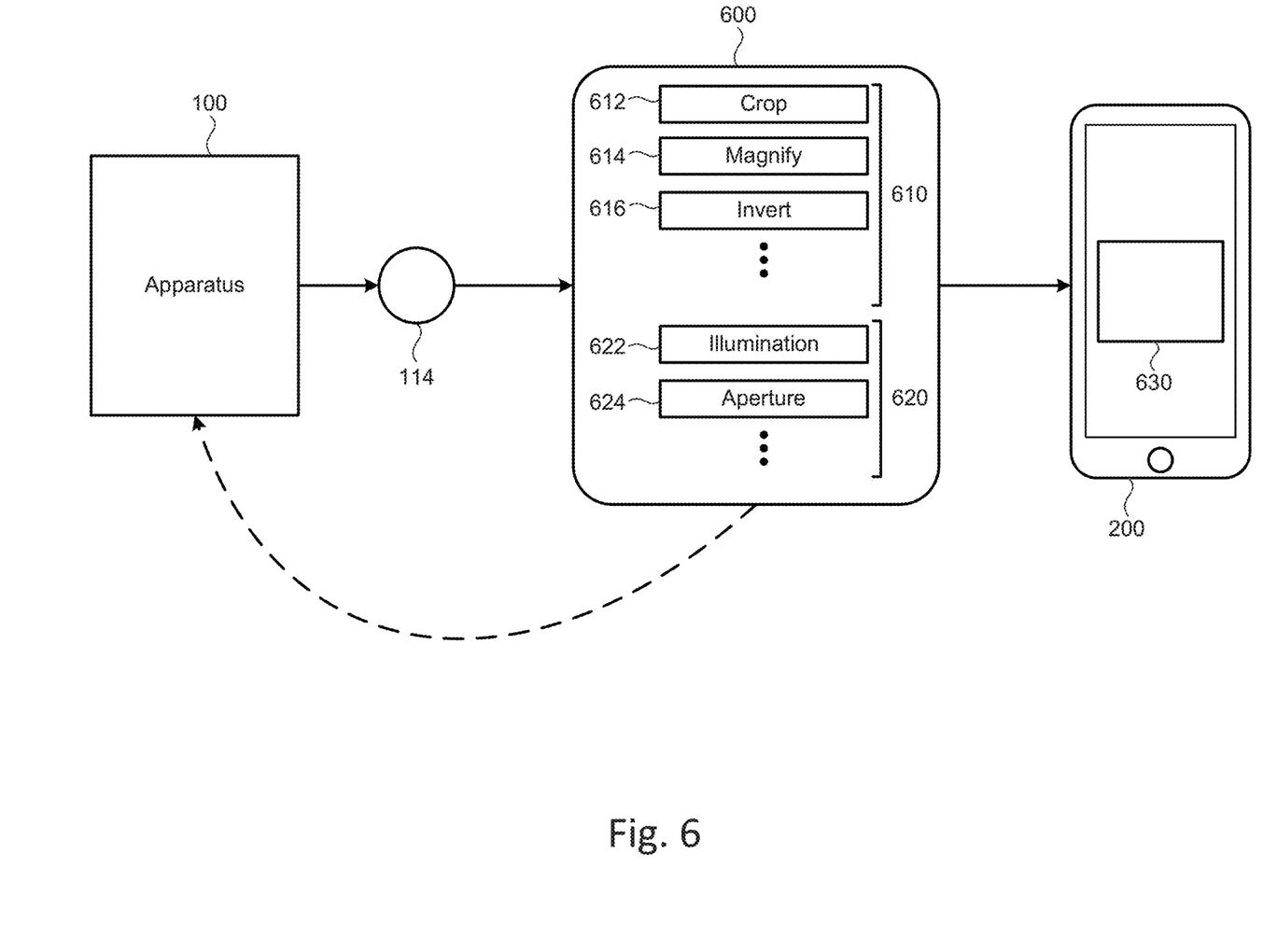
FIG. 6 shows a schematic diagram of an application performing image operations.

With reference to FIG. 6, an application 600 operable with all previous embodiments will now be described. The application 600 receives the final image 114 in a digital format via one or more image sensors of the camera 202 of the mobile user device 200. The application 600 is configured to perform any number of a selection of operations 610 on the image to produce an output image 630. Via the graphical user interface of the mobile user device 200, the application 600 displays the output image 630 on a screen. In addition, the application 600 is operable to effect configuration changes in the apparatus 100 using any number of a selection of configuration controls 620. The application 600 therefore allows for further digital image enhancement and can be used to optimally display the image 114 of the object 102 for the user.

In one example, the operations 610 include cropping 612, digital magnification 614 and/or real-time image inversion 616. Cropping 612 and digital magnification 614 allow the area of interest in the image 114 to be maximised on the screen. The magnification 614 can over-zoom the image, i.e. enlarge it beyond a one-to-one mapping between sensor pixels in the camera 202 and screen pixels. The optical elements of the apparatus 100 may be configured such that the final image shows an inverted version of the object 102. Real-time image inversion 616 allows for this misrepresentation to be corrected.

In another example, the configuration controls 620 include controlling the illumination 622 of the object 102 and the aperture 624 of the optics in the apparatus 100. The illumination control 622 communicates with the lighting arrangement 400 via the electronic circuitry 502, 506, for example to alter the intensity, frequency or beam width of the powered light source 410. The aperture control 624 adjusts the diameter of one or more adjustable apertures present in the apparatus 100, such as the aperture stop 310 or internal apertures of the camera 202 of the mobile user device 200. The skilled person will appreciate that other adjustable elements of the apparatus 100 may be controlled by the application 600 by way of appropriate electro-mechanical communication. Equally, the application may be implemented without configuration controls 620.

In all of the above embodiments and examples, some or all of the magnification may be implemented with optical elements other than lenses, such as mirrors and/or prisms. Optical elements (including lenses, mirrors and prisms) of a sufficient quality are used such that the optical performance of the apparatus 100 is assumed to be diffraction-limited. Effects such as field curvature and geometric distortions are not of importance provided sufficiently small field angles are used, as described above.

The apparatus 100 may be used for a range of other medical examination procedures other than that of the ear canal. For example, the apparatus 100 may be used to inspect the nose, throat and mouth, including for assisting with dental procedures. The apparatus 100 may also be used for external examination, such as that of the eye or skin surface, for which specialised attachments such as restraints or supports may be required. For different specific use cases, different bodies for defining an aperture may be provided at the distal end of the spacing element. For example, a speculum designed for use in a patient's mouth or a body that defines an aperture through which the surface of a patient's skin may be inspected are envisaged. The apparatus can be used equally for veterinary as well as for human medical applications.

While many of the above examples are directed towards medical examination, the apparatus 100 as described may equally be used for a range of applications in other industries. These may include but are not limited to manufacturing quality control, inspecting electronic circuitry and examining items for forensic purposes. The apparatus 100 can be used for detecting surface defects such as cracks in manufactured materials as part of quality control processes. Alternatively, physical and biological items in can be examined non-invasively for forensic investigation using the described apparatus 100.

While a specific architecture is shown, any appropriate hardware or software architecture may be employed. The above embodiments and examples are to be understood as illustrative examples. Further embodiments, aspects or examples are envisaged. It is to be understood that any feature described in relation to any one embodiment, aspect or example may be used alone, or in combination with other features described, and may also be used in combination with one or more features of any other of the embodiments, aspects or examples, or any combination of any other of the embodiments, aspects or examples. Furthermore, equivalents and modifications not described above may also be employed without departing from the scope of the invention, which is defined in the accompanying claims.

The invention claimed is:

1. Apparatus for providing magnification of an object for a device having a camera, the apparatus comprising:
    a first optical element arranged at a first location to provide an image of the object in an intermediate image plane;
    a second optical element arranged at a second location to magnify optically the intermediate image to provide a final image in a final image plane;

means for mounting the apparatus in a fixed position relative to the device such that a camera aperture of the device is supported in the final image plane;

a spacing element for maintaining the first optical element at a fixed distance from the object; and a mirror arrangement comprising a plurality of mirrors to divert the optical path away from and then towards an axis extending between the first optical element and the final image plane, such that the optical path is longer than the distance between the first optical element and the final image plane;

wherein the intermediate image plane and the second optical element are arranged along an optical path extending between the first optical element and the final image plane;

wherein the second optical element is disposed on the optical path between the intermediate image plane and the final image plane;

wherein a first distance along the optical path from the intermediate image plane to the final image plane is significantly smaller than a second distance along the optical path from the first optical element to the intermediate image plane.

2. The apparatus according to claim 1 wherein the device having a camera comprises a mobile user device.

3. The apparatus according to claim 1, further comprising:
a body for defining an aperture through which an object, is examined;
wherein the body is a speculum for placing in a patient's ear canal.

4. The apparatus according to claim 3, wherein the apparatus comprises an otoscope.

5. The apparatus according to claim 3, wherein the speculum is disposed at the distal end of the spacing element, and wherein the spacing element is configured to provide a gap for tool access to the ear canal through the speculum.

6. The apparatus according to claim 1, further comprising:
a third optical element disposed on the optical path in the intermediate image plane, wherein:
the third optical element contains the entire image at the intermediate image plane; and
the third optical element is arranged such that the first optical element and the second optical element lie in conjugate planes.

7. The apparatus according to claim 1, wherein the first optical element comprises two doublets.

8. The apparatus according to claim 1, further comprising:
an aperture stop disposed on the optical path, wherein the aperture stop effects a reduction in the diameter of the entrance pupil of the apparatus, wherein the first optical element comprises two doublets and the aperture stop is disposed between the two doublets.

9. The apparatus according to claim 1, wherein the plurality of mirrors diverts the optical path to a plane substantially parallel and proximate to a distal surface of the device.

10. The apparatus according to claim 1, wherein the first optical element is achromatic.

11. The apparatus according to claim 1, wherein the front focal length of the first optical element is no less than around 80 mm—and no greater than around 180 mm.

12. The apparatus according to claim 1, wherein the power of the second optical element is no less than around 3 dioptres and no greater than around 25 dioptres.

13. The apparatus according to claim 1, wherein the optical magnification factor of the apparatus is no less than around 8.

14. The apparatus according to claim 1, further comprising:
a lighting arrangement comprising a powered light source.

15. The apparatus according to claim 14, further comprising:
an optical arrangement configured to guide light from the powered light source towards the object.

16. The apparatus according to claim 15, the lighting arrangement further comprising:
electronic circuitry for controlling the powered light source; and
an attaching structure for attaching the powered light source and the electronic circuitry to the spacing element;
wherein the optical arrangement comprises a collimator.

17. The apparatus according to claim 16, further comprising:
a handle;
wherein the power source and electronic circuitry for controlling the power source are disposed in the handle.

18. An application for a mobile computing device having a camera receiving an image from the apparatus according to claim 1, the application configured to:
crop the image;
digitally magnify the image; and/or
invert the image in real-time.

19. The application according to claim 18, wherein the apparatus further comprises a lighting arrangement comprising a powered light source, the application further configured to:
control the intensity, frequency and beam width of the powered light source; and
control the diameter of one or more apertures in the apparatus.

* * * * *